United States Patent [19]
Munari et al.

[11] Patent Number: 5,252,109
[45] Date of Patent: Oct. 12, 1993

[54] GAS CHROMATOGRAPHIC INJECTOR

[75] Inventors: Fausto Munari, Milan; Pier Albino Colombo, Castel Cerreto-Treviglio, both of Italy

[73] Assignee: Carlo Erba Strumentazione S.p.A., Milan, Italy

[21] Appl. No.: 872,430

[22] Filed: Apr. 23, 1992

[30] Foreign Application Priority Data

Apr. 24, 1991 [IT] Italy ............ MI91 A 001140

[51] Int. Cl.⁵ .................................... B01D 15/08
[52] U.S. Cl. .................................... 95/87; 95/89; 96/105
[58] Field of Search .............. 55/67, 197, 208, 386

[56] References Cited

U.S. PATENT DOCUMENTS

| | | | |
|---|---|---|---|
| 3,352,089 | 11/1967 | Modell et al. | 55/67 |
| 3,656,277 | 4/1972 | Slingerland | 55/67 |
| 3,778,975 | 12/1973 | Deans | 55/197 |
| 3,881,892 | 5/1975 | Gehrke et al. | 55/67 |
| 4,035,168 | 7/1977 | Jennings | 55/197 X |
| 4,123,236 | 10/1978 | Hirschfeld et al. | 55/197 |
| 4,124,358 | 11/1978 | Müller | 55/67 |
| 4,180,389 | 12/1979 | Paul | 55/208 |
| 4,269,608 | 5/1981 | Sisti et al. | 55/67 |
| 4,422,860 | 12/1983 | Feinstein | 55/67 |
| 4,474,588 | 10/1984 | Hinshaw, Jr. | 55/197 |
| 4,559,063 | 12/1985 | Munari et al. | 55/67 |
| 4,704,141 | 11/1987 | Krebber | 55/197 |
| 4,734,107 | 3/1988 | Trestianu et al. | 55/67 |
| 4,948,389 | 8/1990 | Klein et al. | 55/67 X |
| 5,032,151 | 7/1991 | Klein et al. | 55/67 X |

FOREIGN PATENT DOCUMENTS 62-083660 4/1987 Japan .................... 55/67

*Primary Examiner*—Robert Spitzer
*Attorney, Agent, or Firm*—Millen, White, Zelano & Branigan

[57] ABSTRACT

An injector with a vaporization chamber for gas chromatographic apparatus includes a heater to heat the chamber and a pierceable septum to seal an end of the chamber. At least a heat conducting element is removably mounted between the septum and the heater. One or more elements are positioned adjacent to the septum and are in fluid communication with a source of carrier gas and a discharge outlet. The elements define paths with forced run for washing the septum and for feeding the vaporization chamber.

15 Claims, 4 Drawing Sheets

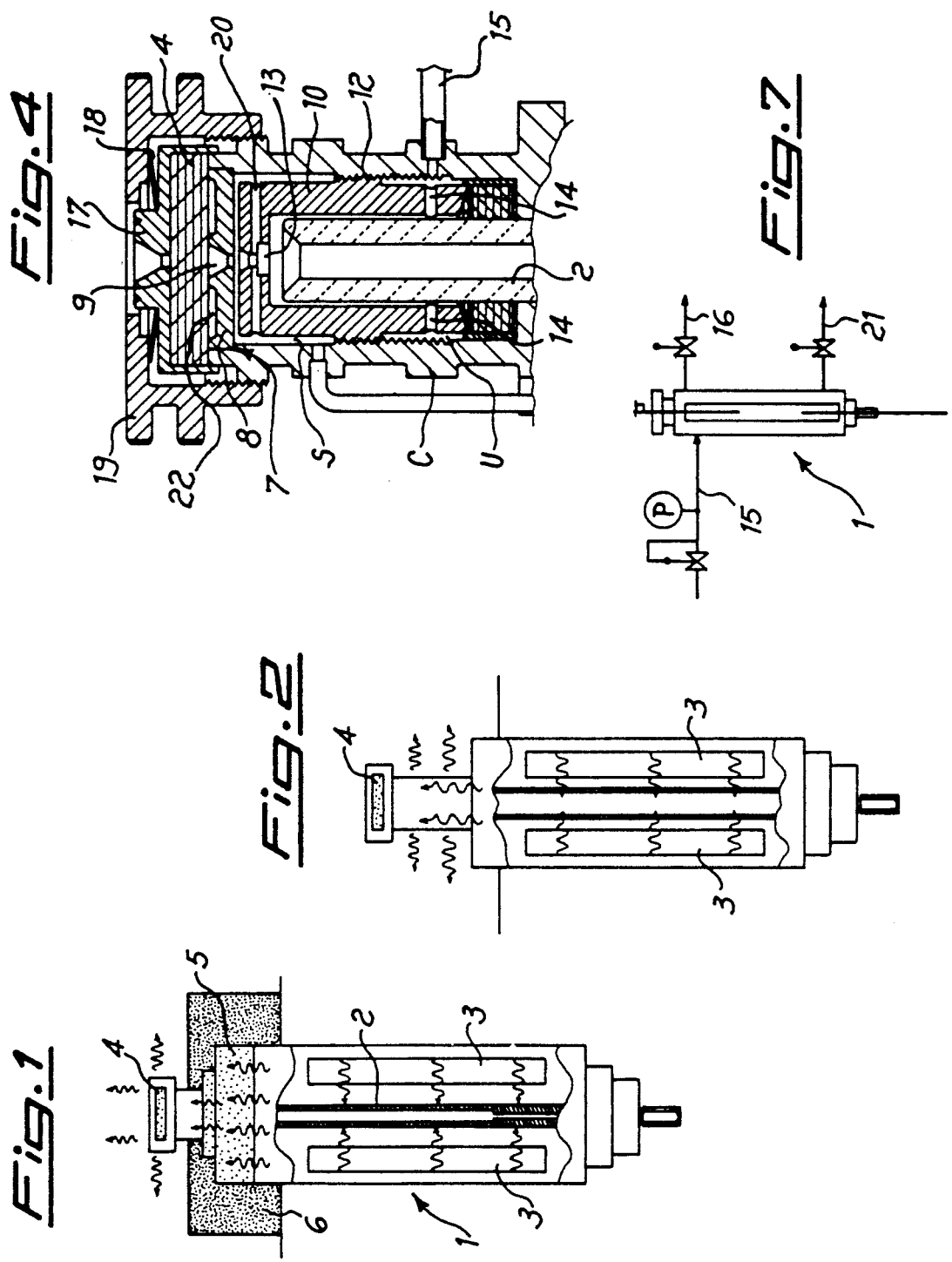

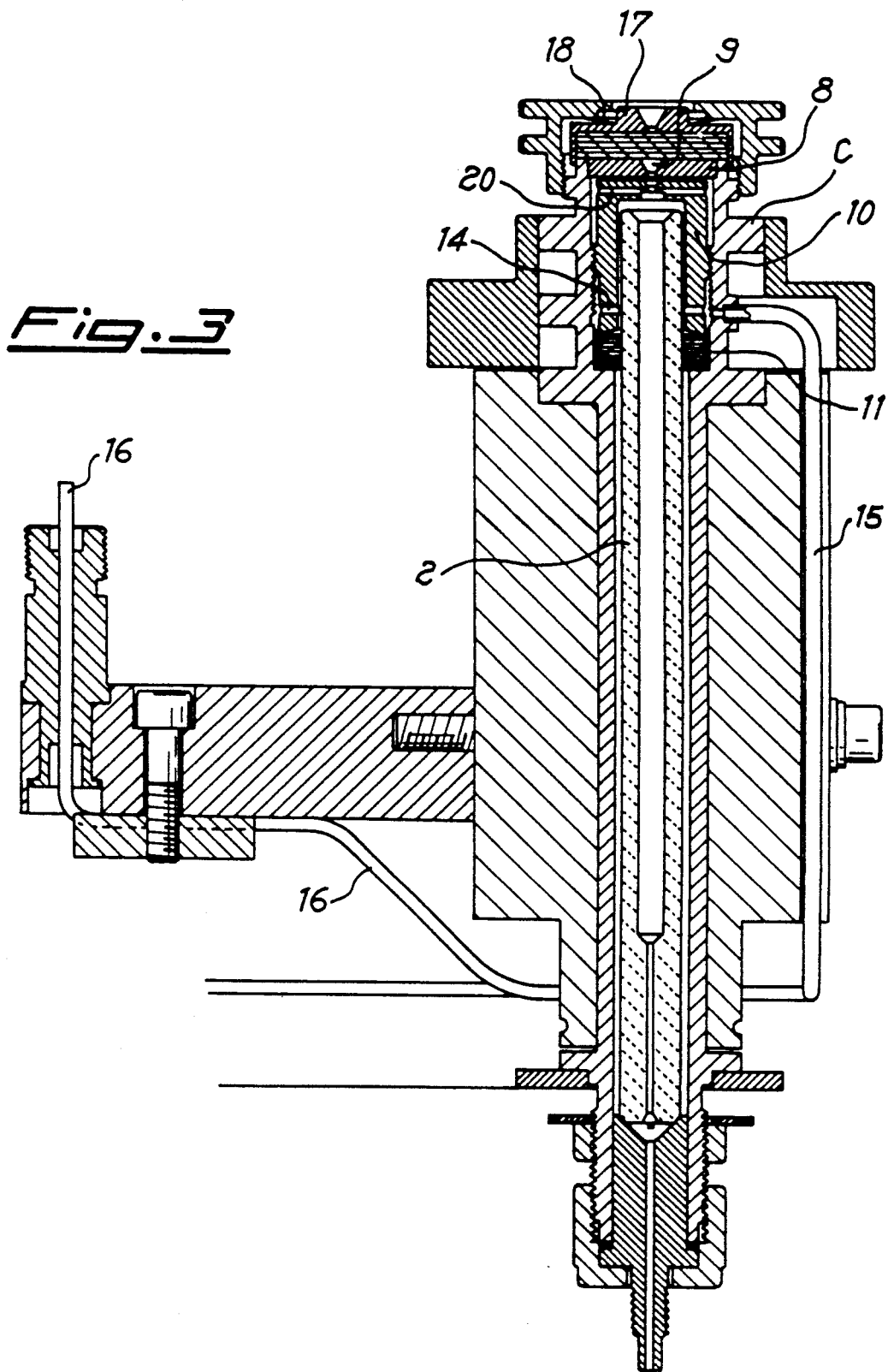

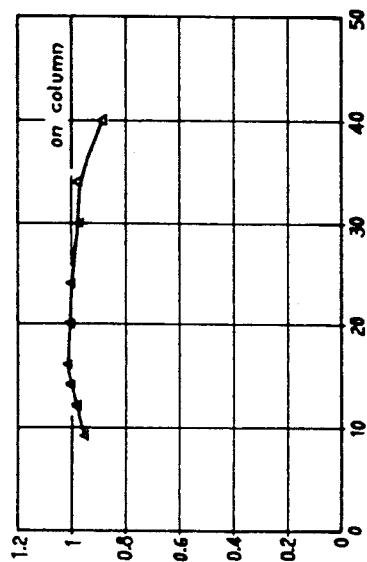
Fig.5
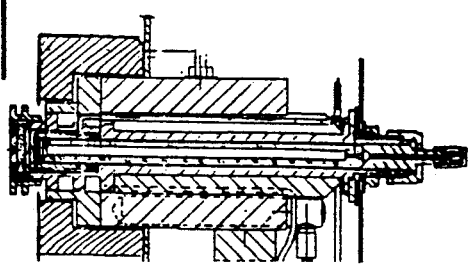
Fig.5A
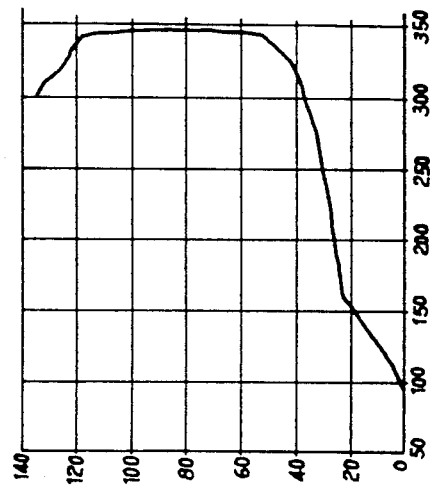
Fig.8
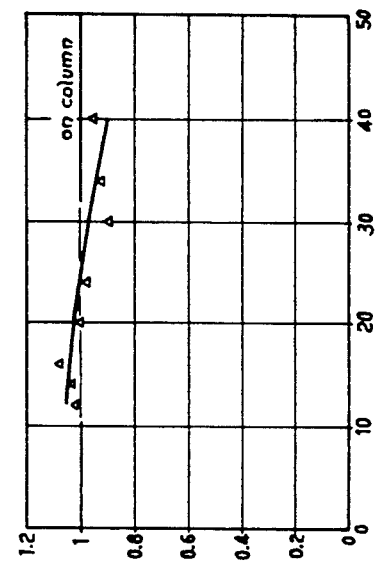
Fig.6
Fig.6A
Fig.9

GAS CHROMATOGRAPHIC INJECTOR

FIELD OF THE INVENTION

The present invention concerns a gas chromatographic injector.

More particularly, the invention concerns an injector of the type with vaporisation chamber, specially for the injection of samples into a capillary gas chromatograph.

DESCRIPTION OF THE PRIOR ART

Injectors of this type have been known for long time in the technique and substantially consist of a chamber provided with heating means and two opposite openings. The upper opening is closed by a septum to be pierced by the needle of a syringe or a sampling device. The lower opening accomodates an end portion of a column or precolumn whose major length is housed inside a gas chromatograph oven.

There are also means for feeding a carrier gas in order to convey the vaporised sample from the injector to the column and the detector.

Though widely known, the injectors with vaporisation chamber present several drawbacks, and in particular that of an incomplete vaporisation of the sample injected into the chamber due to temperature differences existing therein. This problem is particularly relevant when all the injected sample has to be introduced into the separation column, namely in an injection of the "splitless" type, where discrimination between high-boiling and low-boiling compounds is more marked.

Another typical drawback of the injectors with vaporisation chamber is a direct consequence of the nature itself of the septum, which, since it has to be pierced by the injection needle, presents a maximum temperature limit at which it can be submitted, otherwise its physical degradation occurs.

This fact, and the ensuing reduced temperature in the vicinity of the septum involve the possible presence of condensates on the septum itself, condensates that release in time vapours polluting the samples injected afterwards. Furthermore, at relatively high temperatures the septum, though not degrading, releases components that pollute the injected samples.

OBJECTS OF THE INVENTION

An object of the present invention is therefore to solve the abovementioned problems by means of an injector with vaporisation chamber that reduces at a minimum the discrimination between the compounds of the injected sample and at the same time prevents the possible pollution of said sample caused by the septum.

A further object of the invention is to provide a method for the vaporisation injection of samples in gas chromatographic analysis.

SUMMARY OF THE INVENTION

Said objects are achieved by the present invention that concerns an injector with vaporisation chamber for gas chromatography, of the type comprising a sample vaporisation chamber, means to heat said chamber and a pierceable septum to sealingly close an end of said chamber, positioned at a distance from said heating means, characterized in that it further comprises:

- at least a heat conductive element and/or at least a thermally insulating element mounted in a removable way between said septum and said heating means; as well as one or more elements positioned adjacent to said septum and in fluid communication with a source of carrier gas and a discharge outlet, said elements defining forced paths for washing said septum and respectively for feeding said vaporisation chamber.

The invention moreover concerns a method for the vaporisation injection of a sample into a gas chromatographic equipment provided with an injector of the afore described type, characterized in that a reduced flow of washing gas with forced run is fed in correspondence to said septum and/or to the top end of said vaporisation chamber,

- in that one or more heat conductive elements and/or one or more insulating elements are positioned on the top end of the injector, when operating in an injected sample splitless mode, to heat the upper portion of the injector, adjacent to the septum;
- and in that said conductive and/or insulating elements are removed when operating in an injected sample splitting mode.

According to an advantageous feature of the invention, the injector comprises one or more insulating elements to be positioned in a removable way on the heat conductors to improve heating of the end portion of the injector.

According to a further advantageous feature of the invention the internal face of the septum is engaged by a flange provided with an opening having such a size as to substantially allow the passage of an injection needle only, so as to limit to a minimum the free area of the septum inside the injector.

The invention will be now described more in detail with reference to the accompanying drawings given for illustrative and not limiting purposes.

BRIEF DESCRIPTION OF THE DRAWINGS

FIGS. 1 and 2 are side schematic views, partially in section, of an injector according to the invention;

FIG. 3 is a longitudinal section of the injector of FIG. 1;

FIG. 4 is a magnified view of the upper portion of FIG. 3;

FIGS. 5 and 6 are graphs of the thermal profiles of the embodiments of FIGS. 1 and 2, respectively;

FIGS. 5A and 6A are longitudinal sections of the injector of FIGS. 1 and 2, respectively, associated with the graphs of FIGS. 5 and 6, respectively.

FIG. 7 is a diagram of the fluid circuit of an injector according to the invention; and FIGS. 8 and 9 are graphs illustrating the discrimination of compounds of the injected samples, as a function of their molecular weight.

DESCRIPTION OF THE PREFERRED EMBODIMENTS

Figure 10:
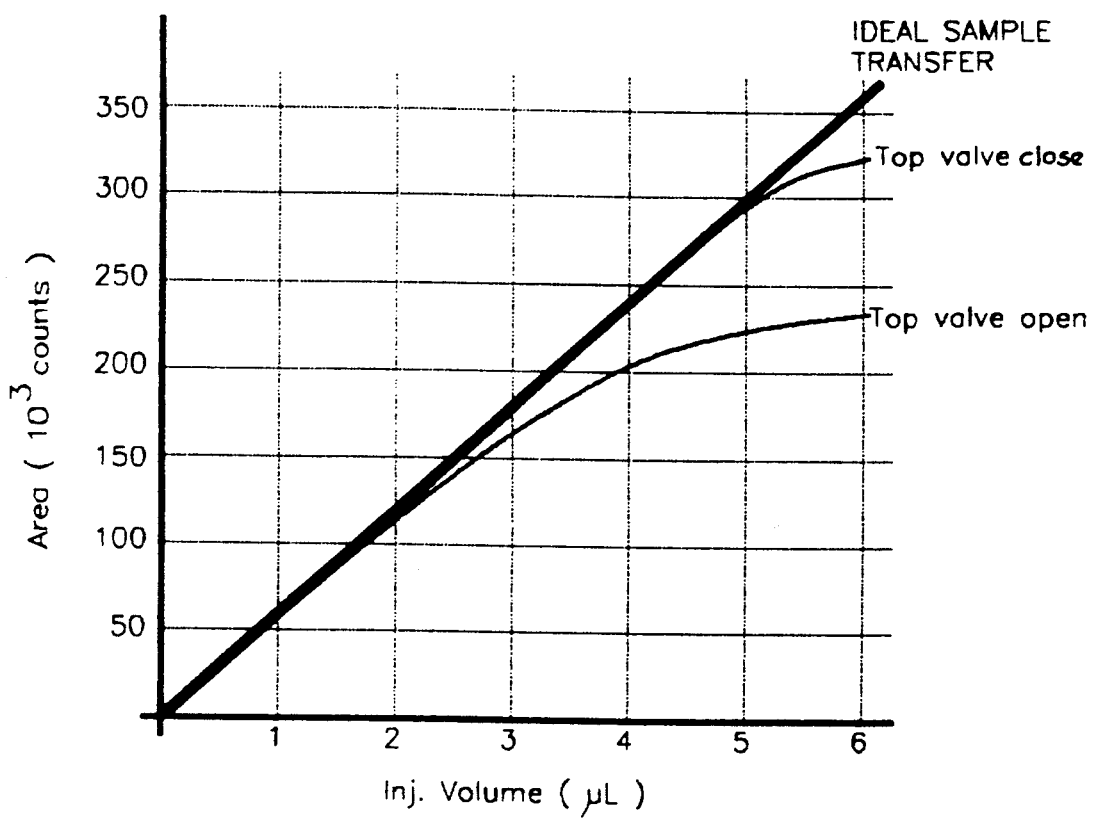
FIG. 10 is a graph showing the influence of flow through the septum flushing line on sample transfer.

Referring first at all to FIG. 1, the injector 1 according to the present invention comprises a vaporisation chamber 2, means 3 to heat the chamber 2, and a septum 4, which has the function of sealingly closing an end of the injector and is made by a material adapted to be pierced by the needle of a syringe or of a sampler for sample injection. As it can be noticed, the septum 4 is at a certain distance from the heating means 2.

According to the invention, the injector 1 further comprises at least a heat conductive element 5 mounted in a removable way on the injector, between the septum 4 and heating means 3. The injector preferably further comprises one or more thermally insulating elements 6, positionable in a removable way on the heat conductors 5 to improve the heating of the upper portion of the vaporisation chamber, or, as an alternative, on the injector upper part in order to improve the heating of this injector part by the usual heating means 3, in case the heat conductors 5 are not present. In this way a thermal profile such as the one shown in FIG. 5 is obtained, where abscissae report the temperature in C degrees and the ordinates the height in millimeters of the temperature detecting point from the injector bottom. In the equipment used to obtain these graphs, the heating elements 3 were set at a temperature of 350 C. degrees and the oven at 50 C. degrees.

For immediate data display, on the right side of the graph of FIG. 5, a corresponding section of the injector 1 is reported as is seen in FIG. 5A.

As it can be noticed, the thermal profile of the injector area approximately corresponding to the vaporisation chamber is substantially flat, and moves away at its upper and lower ends, namely in correspondence with the septum and oven.

FIG. 6 shows the corresponding graph of the thermal profile of an injector as is seen in FIG. 6A according to the invention, but without the element 5 and insulating element 6. As it will be discussed more in detail later on, this configuration, as shown in FIG. 2, can be used in an operative method in which a splitting of the injected sample is foreseen.

A thermal profile substantially intermediate between those of FIGS. 5 and 6 is obtained when the insulating element 6 is present, without heating element 5.

The injector 1 moreover comprises (FIGS. 3 and 4) a plurality of elements positioned adjacent to the septum 4 and in communication with a source of carrier gas and with a discharge outlet, said elements defining a so-called "washing" path of the septum and/or of the corresponding (upper) end of chamber 2, by the carrier gas.

As it can be seen in FIG. 3, one of the elements contributing to form the "washing" path consists of a flange 8 engaging the internal face of the septum 4 and resting on a shoulder or annular projection 7 provided on the injector body. The flange 8 is provided with an opening 9 reduced in size, that is of such size as to substantially allow only the passage of a needle for the sample injection. In this way the septum area that is left free by the opening 9 is in fluid communication with the washing path.

Below the flange 8, and slightly spaced therefrom, a bushing 10 is provided for accomodating the upper end of the vaporisation chamber 2. Preferably, as described hereinbelow, the vaporisation chamber 2 is formed by a liner, generally made of glass, interchangeably housed inside the body C of the injector 1. The bushing 10 is forced with its lower part onto a seal 11 and sideways engages the body C of the injector thanks to a projecting threading 12, thus defining an upper annular space S and a lower annular space U for the carrier gas passage actually without communication between each other. Furthermore, the bushing 10, by stressing the seal 11 against the liner 2, ensures a gas tightness and a correct positioning of said liner.

The bushing 10 is provided in its upper portion with at least a diametral through duct 20 and a central opening 13 similar and coaxial to the opening 9. In its lower end the bushing 10 is provided with radial holes 14 that connect the annular space U to the corresponding internal annular space between bushing and chamber 2.

The carrier gas coming from the feeding duct 15 follows two different paths.

At the beginning the carrier flow penetrates through the space U, the radial holes 14 and passes through the annular space present between the bushing 10 and the chamber 2 as far as the end of said chamber. Most of the carrier gas flows therefrom inside the chamber 2 and from there into the chromatographic column. The remaining portion of carrier gas flows simultaneously partly through the duct 20 into the upper annular space S and partly, through the opening 13 and the space between bushing 10 and flange 8, into the opening 9, thus licking the exposed portion of septum. From here, passing again through the space between flange 8 and bushing 10, the carrier gas flows into the annular space S and from this to a discharge line, not shown in FIG. 4 and indicated by the reference 16 in FIG. 7.

Now it must be noticed that, thanks to the presence of the space between flange 8 and bushing 10, the differences of fluid resistance between the afore described washing path and the vaporisation chamber are such that the portion of carrier gas following the washing path has a forced run towards the discharge line 16 and the washing carrier gas substantially does not enter the vaporisation chamber 2. As it can be seen in FIGS. 3 and 4, the external face of the closing septum 4 is engaged by a further flange 17 provided with an opening of reduced size capable of allowing the needle passage for sample injection and positioned coaxially to the corresponding openings 9 and 13 of the flange 8 and bushing 10. The flange 17 is elastically stressed against the septum 4 by a couple of springs 18 which on its turn cooperates with a nut 19 screwable on the injector body. As it can be seen in FIG. 4, the nut 19 has a conical opening to allow centering automatic sampler devices on the shown injector.

In order to obtain the best operating conditions of septum 4, the flange 8 has a central part 22 of reduced thickness in order to reduce the contact surface between flange and septum. This reduces the possible septum degradation at high temperatures and avoid any "glueing" of septum on the flange metallic surface.

The springs 18 are able to compensate for any size variation of septum due to injector temperature variations, without loosing the pneumatic seal in case of negative temperature gaps and avoiding a too high septum compression in case of positive temperature gaps.

As previously mentioned, the vaporisation chamber 2 can be connected to a splitting line 21 (FIG. 7) by means of known valves that can be controlled to operate according to a split mode or to a splitless mode.

In order to improve the switching from the split configuration to the splitless one, the chamber 2 is formed by interchangeable liners having variable diameter and internal configuration according to the operative mode. More particularly, when operating in splitless mode, a liner with relatively reduced internal diameter is used, said liner having a terminal restriction (FIGS. 1 and 3); when operating in split mode, a liner with higher internal diameter and without restriction is used (FIG. 2).

The method for the vaporisation injection of a sample in a gas chromatographic equipment provided with an injector of the afore described type foresees to feed a reduced flow of washing gas in correspondence to the septum 4 and/or to the upper end of chamber 2 with forced run through the previously shown path. Simultaneously, according to the operative conditions used, the upper portion of the injector and of the vaporisation chamber will be heated or not. When operating in sample splitless mode, said upper portion is heated by means of the heat conductive element 5 and the insulating element 6.

When operating in sample split mode, the elements 5 and 6 are removed thus obtaining the thermal profile of FIG. 6. In the latter case the vaporisation chamber 2 consists of a liner of a relatively high diameter to improve an optimized mixing between the carrier gas and the vapours of the injected compound even in absence of glass wool or similar mixing means.

FIGS. 8 and 9 show two graphs reporting the discrimination between compounds of n-alkane samples as a function of their number of carbon atoms, with respect to a component $C_{20}$ taken as reference, operating in splitless mode and in split mode, respectively. The abscissae report the number of carbon atoms and the ordinates the value obtained by the following formula:

$$(\text{Compound area/compound weight}) \times (\text{Weight } C_{20}/\text{Area } C_{20})$$

The experimental conditions to obtain these graphs are as follows:
Oven temperature: 70 C. (1 min), then up to 320 C. at 10 C./min
Injector temperature: 320 C.
Detector temperature: 350 C.
Carrier: hydrogen at 2.5 ml/min As it is evident from said graphs, the discrimination is very reduced and does not exceed 10% in the worst case. The continuous line in correspondence to the optimal value 1 corresponds to the values as obtained by using an on-column injection technique and is indicated as reference. FIG. 10, shows the sample transfer in splitless conditions when the top valve, controlling the septum flushing line, is kept closed or respectively opened.

We claim:

1. A method for splitless vaporization injection of a sample in gas chromatographic equipment wherein an injector comprising a vaporizing chamber having an upper portion is provided with interchangeable internal liners, heating means to heat said vaporizing chamber, a needle pierceable septum sealingly closing said vaporizing chamber and spaced from said heating means, heat conducting means or thermal insulating means removably connectable to said gas chromatographic equipment between said septum and said heating means, and a plurality of elements provided adjacent to said septum, within said vaporizing chamber and in fluid communication with a source of carrier gas and a discharge outlet, said elements defining paths with forced run for washing said septum and for feeding said vaporizing chamber, respectively, the method comprising the steps of: heating said vaporizing chamber to a vaporizing temperature of the sample to be injected, connecting said heat conducting means or thermal insulating means to said gas chromatographic equipment between said septum and said heating means to heat the upper portion of said vaporizing chamber, feeding a carrier gas through said paths to wash said septum and feeding said carrier gas to the vaporizing chamber, and injecting said sample into said vaporizing chamber.

2. A method according to claim 1, wherein different liners are used in split and in splitless injection modes.

3. A method according to claim 1, wherein said flow of carrier gas through said discharge outlet is discontinued when the equipment is operating in a splitless mode.

4. A method for split vaporization injection of a sample in gas chromatographic equipment wherein an injector comprising a vaporizing chamber is provided with interchangeable internal liners, heating means to heat said vaporizing chamber, a needle pierceable septum sealingly closing said vaporizing chamber and spaced from said heating means, heat conducting means or thermal insulating means removably connectable to said gas chromatographic equipment between said septum and said heating means, and a plurality of elements provided adjacent to said septum, within said vaporizing chamber and in fluid communication with a source of carrier gas and a discharge outlet, said elements defining paths with forced run for washing said septum and for feeding said vaporizing chamber, respectively, the method comprising the steps of: heating said vaporizing chamber to a vaporizing temperature of the sample to be injected, disconnecting and removing said heat conductive means or thermal insulating means from between said septum and said heating means of the gas chromatographic equipment, feeding a carrier gas through said paths to wash said septum and feeding said carrier gas to the vaporizing chamber, and injecting said sample into said vaporizing chamber.

5. A method according to claim 4, wherein different liners are used in split and in splitless injection modes.

6. An injector having a body with a vaporization chamber having an upper end for gas chromatography, of the type comprising a sample vaporization chamber, heating means to heat said chamber and a pierceable septum having an external face and an internal face for sealingly closing an end of said chamber the septum being placed at a certain distance from said heating means, wherein the injector further comprises:
at least a heat conductive means or at least a thermal insulating means mounted in a removable way between said septum and said heating means; as well as at least one element positioned adjacent to said septum and in fluid communication with a source of carrier gas and a discharge outlet, said element defining a path with forced run for washing said septum and for feeding said vaporization chamber, respectively.

7. An injector according to claim 6, characterized in that at least one insulating element is mounted in a removable way on said heat conductive element(s).

8. An injector according to claim 6, wherein the internal face of said closing septum is engaged by at least an internal flange, provided with an opening of reduced size, and wherein the upper end of said vaporisation chamber is accommodated with clearance in a bushing engaged with said injector to define external annular spaces and an internal annular space; said bushing lying at a distance from said flange and being provided with means for connecting said internal and external spaces as well as with an opening similar and coaxial with said flange opening.

9. An injector according to claim 8, wherein said flange engaging the septum internal face has a central portion of reduced thickness to have a contact between flange and septum limited to two annular crowns.

10. An injector according to claim 8, wherein said bushing is screwed on said injector body and in engages at least a seal, stressing the real against said chamber and said injector body.

11. An injector according to claim 8, wherein the external face of said closing septum is engaged by an external flange having a second opening of reduced size and capable of allowing the passage of an injection needle, said second opening being substantially coaxial and corresponding in size to the opening of said internal flange.

12. An injector according to claim 11, wherein said external flange is elastically stressed against said closing septum.

13. An injector according to claim 6, wherein said vaporisation chamber is comprised of a liner interchangeably housed inside the body of said injector.

14. An injector according to claim 6, wherein said vaporisation chamber is connected to one or more splitting lines provided with corresponding, controllably operated valves.

15. An injector according to claim 14, wherein said lines or valves are heated by heat conducting appendices of the injector.

* * * * *